(12) United States Patent
Mogensen

(10) Patent No.: US 11,229,438 B2
(45) Date of Patent: Jan. 25, 2022

(54) IMPLANTABLE MEDICAL DEVICE INCLUDING VALVE MEMBER

(71) Applicant: Cook Medical Technologies LLC, Bloomington, IN (US)

(72) Inventor: John Mogensen, Hvidovre (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 187 days.

(21) Appl. No.: 16/020,448

(22) Filed: Jun. 27, 2018

(65) Prior Publication Data

US 2019/0000483 A1 Jan. 3, 2019

Related U.S. Application Data

(60) Provisional application No. 62/525,998, filed on Jun. 28, 2017.

(30) Foreign Application Priority Data

Jun. 28, 2017 (GB) ...................................... 1710339

(51) Int. Cl.
| | |
|---|---|
| *A61F 2/07* | (2013.01) |
| *A61B 17/12* | (2006.01) |
| *A61B 90/00* | (2016.01) |
| *A61B 17/00* | (2006.01) |
| *A61F 2/24* | (2006.01) |

(Continued)

(52) U.S. Cl.
CPC .......... *A61B 17/12036* (2013.01); *A61F 2/07* (2013.01); *A61B 17/12109* (2013.01); *A61B 17/12172* (2013.01); *A61B 17/12177* (2013.01); *A61B 2017/00876* (2013.01); *A61B 2017/1205* (2013.01); *A61B 2090/3966* (2016.02);

(Continued)

(58) Field of Classification Search
CPC .................................. A61F 2/07; A61B 17/12
See application file for complete search history.

(56) References Cited

U.S. PATENT DOCUMENTS

| | | | |
|---|---|---|---|
| 4,922,905 A | 5/1990 | Strecker | |
| 6,102,938 A | 8/2000 | Evans et al. | |

(Continued)

FOREIGN PATENT DOCUMENTS

| | | |
|---|---|---|
| CN | 203852449 | 10/2014 |
| EP | 2676638 A1 | 12/2013 |

(Continued)

OTHER PUBLICATIONS

Distal False Lumen Occlusion in Aortic Dissection with a Homemade Extra Large Vascular Plug, Kolbel et al, Aug. 2013.

(Continued)

*Primary Examiner* — Matthew W Schall
(74) *Attorney, Agent, or Firm* — Crowell & Moring LLP

(57) ABSTRACT

An implantable medical device includes an elongate support member including an internal wall forming an internal lumen and an elongate flexible tubular valve member having a length, a proximal end, and a closable distal end. The proximal end of the valve member is secured to the support member and is configured to be held open thereby in a deployed condition of the device. The valve member is at least partially unstented along its length. In a deployed condition of the device, flow in a proximal direction causes the distal end of the valve member to be closed.

18 Claims, 10 Drawing Sheets

(51) Int. Cl.
    *A61F 2/90* (2013.01)
    *A61F 2/962* (2013.01)
    *A61F 2/06* (2013.01)

(52) U.S. Cl.
    CPC .............. *A61F 2/2412* (2013.01); *A61F 2/90* (2013.01); *A61F 2/962* (2013.01); *A61F 2002/068* (2013.01)

(56) References Cited

U.S. PATENT DOCUMENTS

| | | |
|---|---|---|
| 6,305,436 B1 | 10/2001 | Andersen et al. |
| 6,926,689 B2 | 8/2005 | Scheule |
| 7,278,430 B2 | 10/2007 | Kumar |
| 8,038,710 B2 | 10/2011 | Fearnot et al. |
| 8,480,726 B2 | 7/2013 | Cunningham et al. |
| 8,906,086 B2 | 12/2014 | Roeder et al. |
| 9,364,354 B2 | 6/2016 | Ben-Muvhar et al. |
| 9,427,233 B2 | 8/2016 | Fearnot et al. |
| 2004/0117004 A1 | 6/2004 | Osborne et al. |
| 2006/0173490 A1 | 8/2006 | Lafontaine et al. |
| 2010/0106240 A1 | 4/2010 | Duggal et al. |
| 2011/0054512 A1 | 3/2011 | Hendricksen et al. |
| 2012/0116496 A1 | 5/2012 | Chuter et al. |
| 2017/0056175 A1 | 3/2017 | Chin et al. |

FOREIGN PATENT DOCUMENTS

| | | |
|---|---|---|
| EP | 18275094.3 | 11/2018 |
| GB | 1710339.1 | 11/2017 |
| WO | 2008097590 A1 | 8/2008 |
| WO | 2008103572 A1 | 8/2008 |
| WO | WO 2008-097590 A1 | 8/2008 |
| WO | WO 2008-103572 A1 | 8/2008 |
| WO | 2016064748 A1 | 4/2016 |
| WO | WO 2016064748 A1 | 4/2016 |
| WO | 2008022327 A2 | 2/2018 |
| WO | WO 2008022327 A2 | 2/2018 |

OTHER PUBLICATIONS

Tilo Kolbel, MD, PhD et al, "Distal False Lumen Occlusion in Aortic Dissection with a Homemade Extra Large Vascular Plug", J Endovasc Ther 2013; 20:484-489.

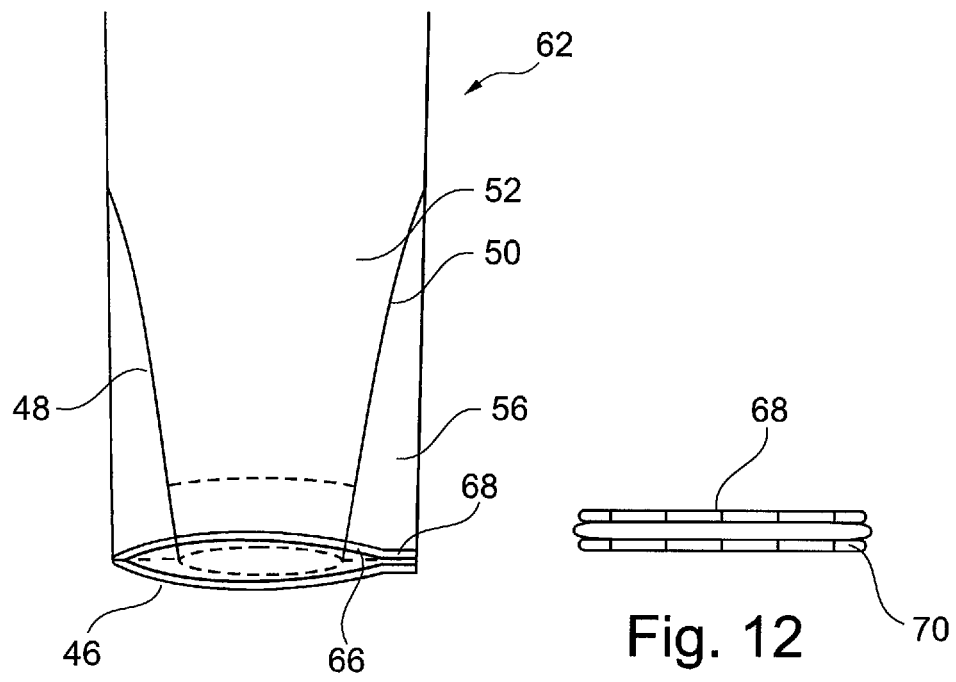
Fig. 11
Fig. 12
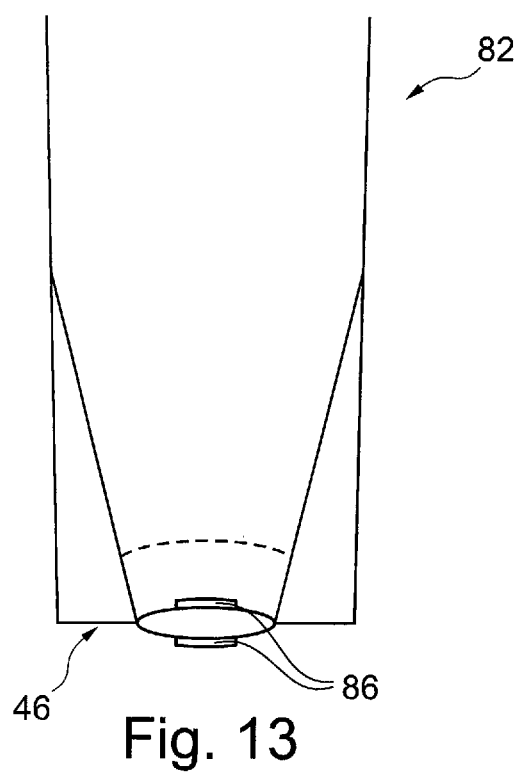
Fig. 13

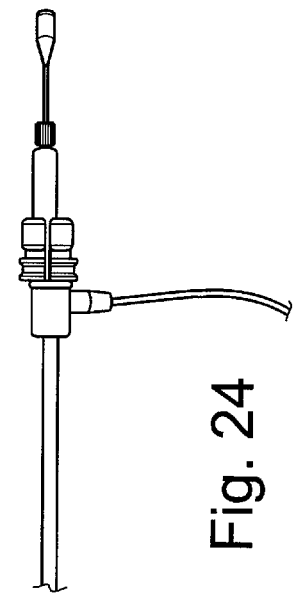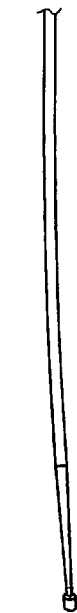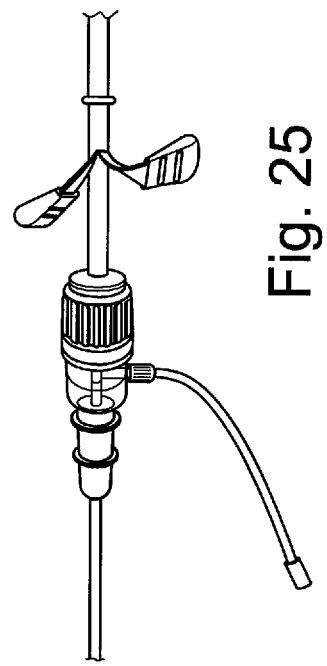
Fig. 23
Fig. 24
Fig. 25
Fig. 26

IMPLANTABLE MEDICAL DEVICE INCLUDING VALVE MEMBER

CROSS REFERENCE TO RELATED APPLICATIONS

This application claims the benefit of Great Britain patent application No 1710339.1 filed on Jun. 28, 2017 and U.S. Provisional patent application No. 62/525,998 filed on Jun. 28, 2017 both entitled "Implantable Medical Device Including Valve Member" the entire contents of which are incorporated herein by reference.

TECHNICAL FIELD

The present invention relates to an implantable medical device including a valve member, for example for a false lumen of dissection.

BACKGROUND OF THE INVENTION

A false lumen caused by a type B aortic dissection may be treated by closing the upstream end of the false lumen for example with a stent graft. However, in some instances, the false lumen can still receive backflow from downstream tears in the false lumen wall.

A conventional way to treat this is to use a candy plug, in particular a candy plug including a valve element.

Some existing documents include U.S. Pat. No. 9,364,354, "Distal False Lumen Occlusion in an Aortic Dissection with a Homemade Extra Large Vascular Plug: The Candy-Plug Technique" by Kolbel et al., J Endovasc Ther. 2013 August; 20(4): 484-9, U.S. Pat. Nos. 7,278,430, 9,427,233, CN203852449, U.S. Pat. No. 6,926,689, WO 2008/097590.

SUMMARY OF THE INVENTION

The present invention seeks to provide an improved implantable medical device.

According to an aspect of the invention, there is provided an implantable medical device, including:

an elongate support member including an internal wall forming an internal lumen; and an elongate flexible tubular valve member having a length, a proximal end, and a closable distal end, the proximal end of the valve member being secured to the support member and configured to be held open thereby in a deployed condition of the device, the valve member being at least partially unstented along its length;

wherein in a deployed condition of the device flow in a proximal direction causes the distal end of the valve member to be closed.

Preferred embodiments provide a plug for preventing backflow through a false lumen of a dissection, which includes a valve which can be readily compressed for delivery and which provides reliable closure of the false lumen preventing backflow of blood thereto.

It is known to use a candy plug to plug backflow from downstream tears in a false lumen wall. However, a problem with some existing candy plug assemblies is that the valve is difficult to compress radially for delivery through an introducer assembly.

Preferred embodiments provide a more effective valve apparatus which can be readily constrained for delivery purposes.

Preferred embodiments are for use at the downstream end of a false lumen to prevent backflow.

Preferred embodiments can be made with conventional stent and graft materials.

In some embodiments, the distal end of the valve member is radially compressible and/or radially foldable.

Preferably, the valve member is secured to the internal wall of the support member, and the distal end of the valve member is preferably loose from the support member.

Preferably, the valve member includes a graft material tube.

In some embodiments, the proximal end of the valve member has a proximal opening and the distal end of the valve member is openable to a maximum distal opening, wherein the maximum distal opening is smaller than the proximal opening.

Preferably, in a deployed condition of the device, the valve member includes a lumen from the proximal end to the distal end, wherein the lumen tapers along at least part of the length of the valve member.

In some embodiments, in a deployed condition of the device, the lumen along the at least part of the length of the valve member is substantially conical.

Some embodiments include first and second lines of attachment along the at least part of the length of the graft material tube, the first and second lines of attachment reducing a size of the lumen in a deployed condition of the device and dividing a wall of the valve member into a first side section and a second side section by attaching opposing points of the valve member, the first and second lines of attachment converging towards the distal end of the valve member.

In some embodiments, at each cross section of the at least part of the length of the valve member, the perimeter sections provided by the first and second side sections are substantially the same size.

The first and second lines of attachment can be provided by stitching.

Some embodiments can include a biasing element configured to bias the distal end of the valve member to adopt a closed configuration. The biasing element can include attracting magnetic elements and/or a resilient member. The resilient member can include first and second wires comprising shape memory material.

In some embodiments, the lumen of the support member has a proximal section proximal of the valve member, the proximal section being in fluid communication with an interior of the valve member. The support member can have a distal section distal of the proximal end of the valve member.

In some embodiments, the internal wall of the support member is unitary with the valve member.

In some embodiments, the device includes a tubular member providing the internal wall of the valve member and being inverted through itself to provide the valve member.

In some embodiments, the support member has a proximal anchoring section, a distal anchoring section, and an attachment support section, wherein the attachment support section is between the proximal anchoring section and the distal anchoring section and has in a deployed condition a smaller diameter than the proximal anchoring section and the distal anchoring section, wherein the proximal end of the valve member is secured to the support member in the attachment support section.

In some embodiments, the support member includes a candy plug.

In some embodiments, the distal end of the valve member is configured to open to allow components of an introducer system to be retracted, and otherwise to be closed.

In some embodiments, the distal end of the valve member is configured to close and to remain closed after components of an introducer system have been retracted.

In some embodiments, the distal end of the valve member is configured to be and remain closed after components of an introducer system have been retracted.

Some embodiments provide a valve arrangement which can be fitted to the inner lumen of a candy plug, this being made of a tubing of graft material which is sewn to have a conical or tapering form. The wide end of the tubing can be sewn to the inside of the candy plug, whereas the narrow, free, end is disposed downstream in the normal direction of bloodflow. When there is backflow the tubing will preferably close to prevent flow of blood back into the false lumen. The free end of the tubing may be provided with nylon fibres for thrombogenic purposes. In some embodiments two magnets may be disposed on opposing sides of the narrow opening of the valve at its free end to close the valve when a cannula, tip and/or wire guide are pulled out. Backflow will preferably cause the valve to close even in the presence of the magnets.

BRIEF DESCRIPTION OF THE DRAWING

Embodiments of the invention are described below, by way of example only, with reference to the accompanying drawings, in which:

FIG. 11 is a schematic view of a valve member of another embodiment of the invention;

FIG. 12 is an end view of the valve member of FIG. 11;

FIG. 13 is a schematic view of a valve member of another embodiment of the invention.

FIGS. 23-26 are views of a delivery device for embodiments of the invention.

DETAILED DESCRIPTION

Described below are preferred embodiments of an implantable medical device constructed according to the teachings herein. It is to be understood that the drawings are not to scale and are intended merely to be illustrative of the features and elements of the device and its components.

Throughout this specification the term proximal with respect with both human or animal vasculature will be used to refer to the region closest to the heart and similarly that part of the implantable medical device which when in use is closest to the heart, while the term distal will be used for the regions of the human or animal vasculature further from the heart and similarly those parts of the implantable medical device which in use are further from the heart. With regard to a deployment or introducer assembly or retrieval device, the term distal is also used to denote the part of the assembly which remains closest to the clinician during the medical procedure, and typically outside the patient, and the term proximal is also used to denote the end of the assembly which is furthest from the clinician and which is first fed endoluminally into the patient's vasculature.

A proximal direction is a direction in which movement would cause an object to assume a more proximal position. A distal direction is a direction in which movement would cause an object to assume a more distal position.

The implantable devices described herein have what could be termed a compressed configuration or a compressed condition for delivery and a deployed configuration or a deployed condition upon implantation. Unless otherwise specified, the description of the devices relates to the deployed condition.

Figure 1:
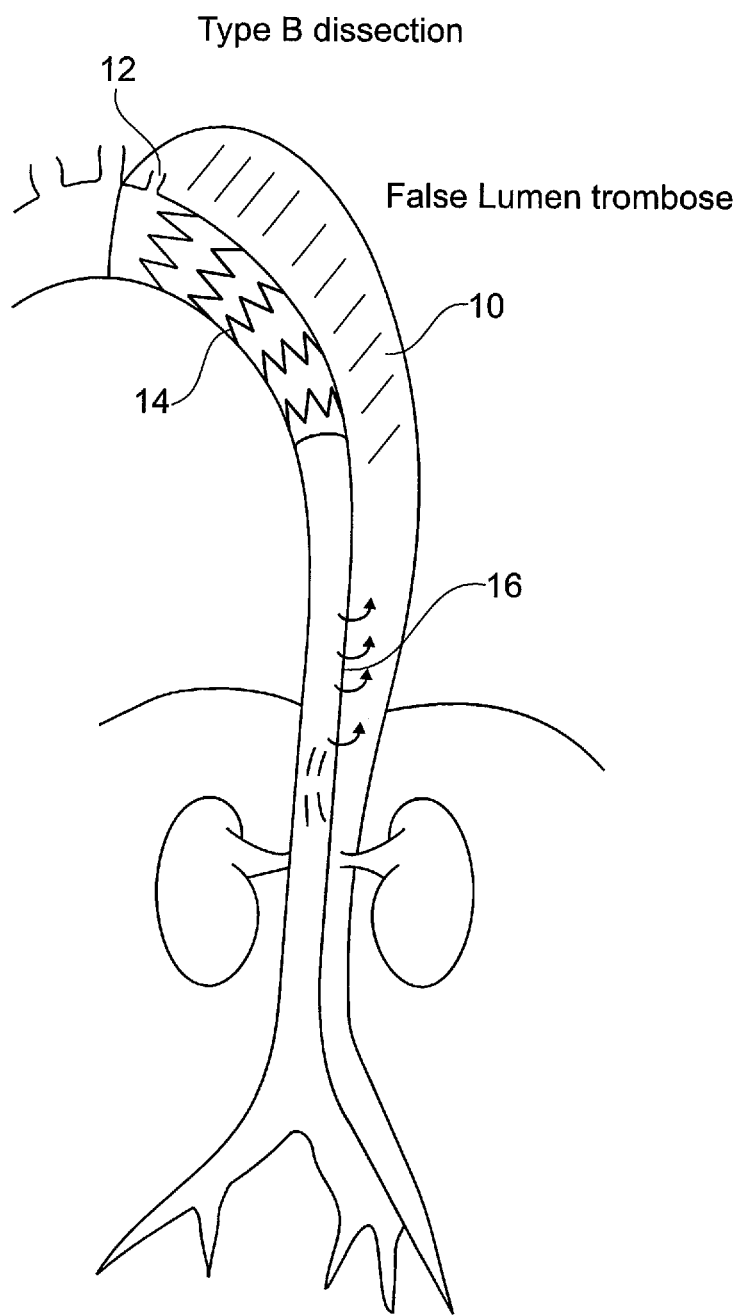
FIG. 1 is a schematic representation of a type B aortic dissection with a false lumen closed at its upstream end.

FIG. 1 shows a representation of a type B aortic dissection which has resulted in a false lumen 10. An upstream tear 12 in the aortic wall has been closed by a stent graft 14. However, the stent graft 14 does not extend all the way to the downstream end of the false lumen.

In this case, there is a downstream tear 16 in the false lumen wall which allows backflow into the false lumen. This can prevent the false lumen from draining and put additional strain on the dissection.

Figure 2:
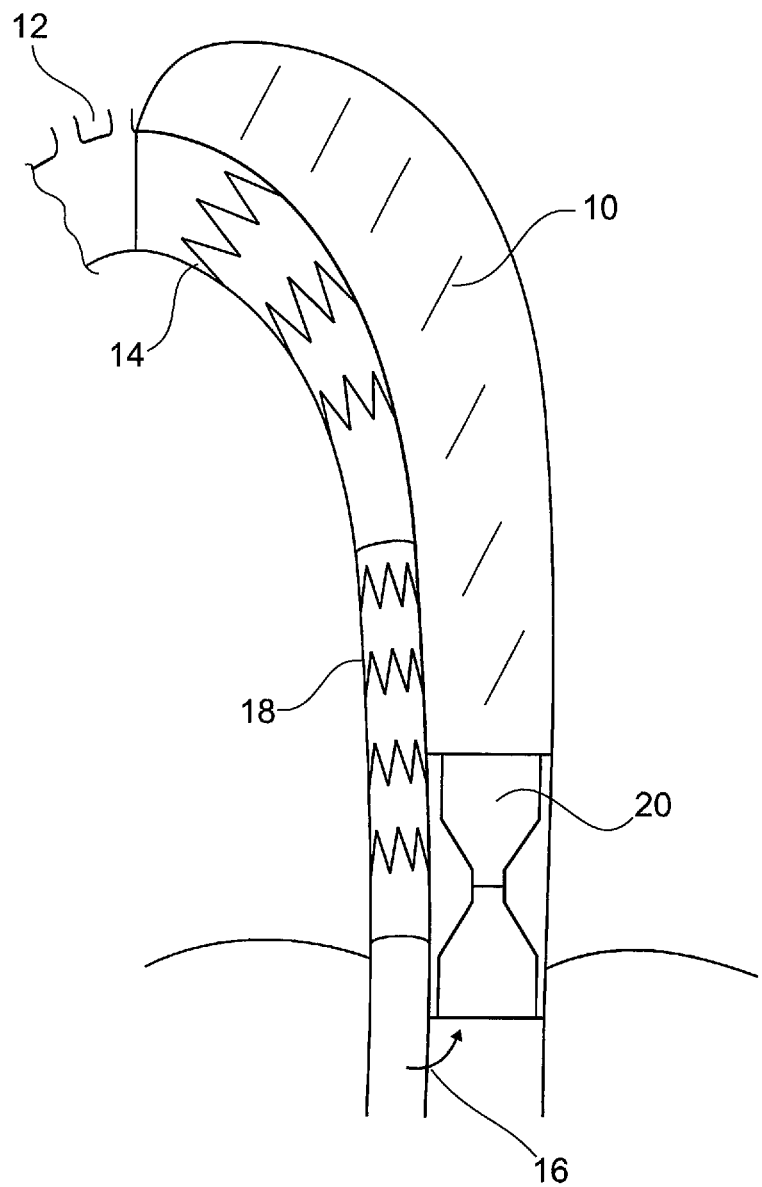
FIG. 2 is a schematic representation of a type B aortic dissection showing how back flow from downstream tears can be plugged using a known candy plug.

FIG. 2 is a representation of a known way of addressing the problem shown in FIG. 1.

As can be seen in FIG. 2, a further stent graft 18 has been deployed downstream of the first stent graft 14 in the aorta. In addition, a candy plug 20 has been deployed in the false lumen.

Figure 3:
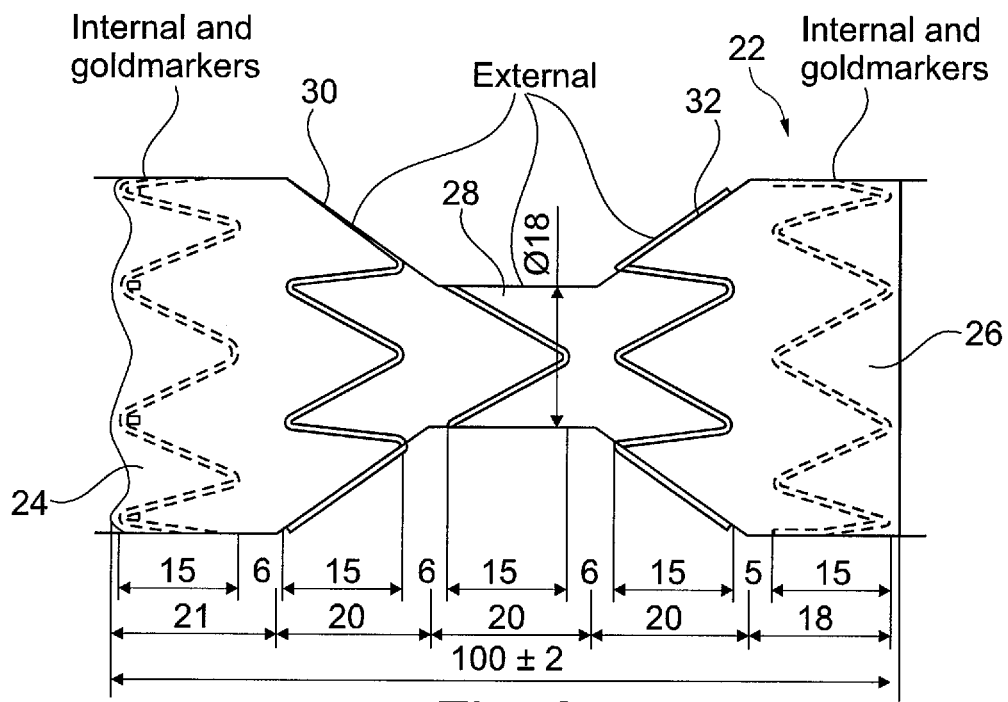
FIG. 3 is a side elevational view of a known candy plug.

The candy plug of this example is shown in more detail in FIG. 3.

As can be seen in FIG. 3, the candy plug includes an elongate support member 22 in the form of a stent graft.

The support member includes a proximal anchoring section 24, a distal anchoring section 26, and an intermediate section 28.

In a deployed condition, as shown in FIG. 3, the intermediate section 28 has a smaller diameter than both the proximal anchoring section 24 and the distal anchoring section 26. The diameters of the proximal anchoring section 24 and distal anchoring section 26 are approximately the same in the device shown in FIG. 3. The smaller diameter of the intermediate section can be caused by a diameter reducing suture.

As can be seen in FIG. 3, the support member also includes a proximal tapering section 30 and a distal tapering section 32. The proximal tapering section 30 connects the proximal anchoring section 24 to the intermediate section 28, and the distal tapering section 32 connects the intermediate section 28 to the distal anchoring section 26.

The proximal tapering section 30 has in the deployed configuration a diameter which tapers from the proximal anchoring section to the intermediate section 28. The distal tapering section 30 has in the deployed configuration a diameter which tapers from the distal anchoring section to the intermediate section 28.

The elongate support member 22 includes an internal wall forming an internal lumen which is continuous through the proximal anchoring section, proximal tapering section, intermediate section, distal tapering section, and distal anchoring section. The intermediate section 28 is between and in fluid communication with the proximal anchoring section 24 and the distal anchoring section 26.

The support member is provided by a graft material tube with, in the device of FIG. 3, 5 stents. A stent is provided on each of the proximal anchoring section 24, the proximal tapering section 30, the intermediate section 28, the distal tapering section 32, and the distal anchoring section 26. The stents on the proximal and distal anchoring sections are, for the support member of FIG. 3, internal, whereas the stents on the tapering sections and on the intermediate section are external. As can be seen from FIG. 3, the stents at the proximal and distal anchoring sections are provided with gold markers.

Figure 4:
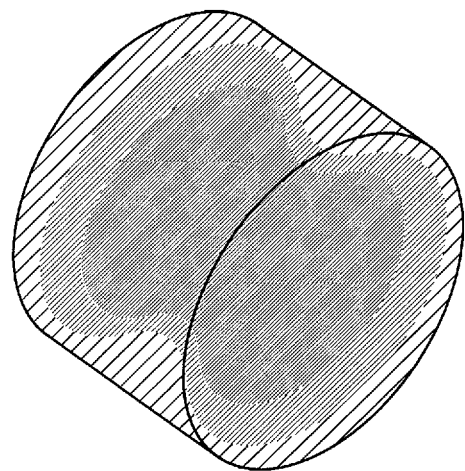
FIG. 4 is a perspective view of a known candy plug.

The support member 22 supports a valve element (shown in FIG. 4; not visible in FIG. 3) to prevent backflow into the false lumen by occlusion of the lumen.

As can be seen in FIG. 2, the candy plug 20 has been deployed in the false lumen adjacent to or upstream of the tear 16 and the valve element can prevent the false lumen from receiving new blood from the tear 16.

However, a problem with some existing candy plug assemblies is that the valve is difficult to compress radially for delivery through an introducer assembly.

A device 40 according to an embodiment of the invention is described with respect to FIGS. 5 to 10.

Figure 5:
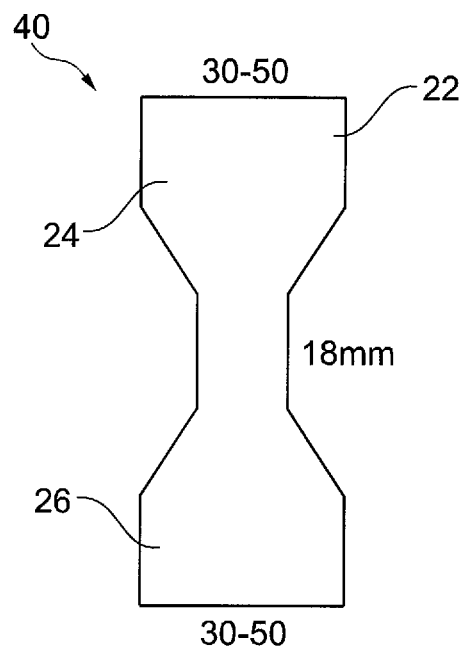
FIG. 5 is a side elevational schematic view of a device according to an embodiment of the invention.

FIG. 5 shows the device 40 including a support member 22 which is the same as the support member shown in FIG. 3 with exceptions detailed below.

The support member of FIG. 5 is not for supporting the same valve as the support member of FIG. 3. Instead, the support member of FIG. 5 supports an elongate flexible tubular valve member 42 shown in FIGS. 6 to 9 and discussed below. The elongate flexible tubular valve member 42 has an open proximal end 44 in a deployed condition of the device and a closable distal end 46. The distal end 46 can be opened, for example to allow retraction of an introducer tip, cannula and/or wire-guide as described below. However, proximal flow for example of blood causes the distal end 46 to be closed to minimise back flow into a false lumen. This can assist blood in the false lumen to thrombose. The elongate flexible tubular valve member is easily radially compressible or foldable for compression into an introducer assembly.

Figure 6:
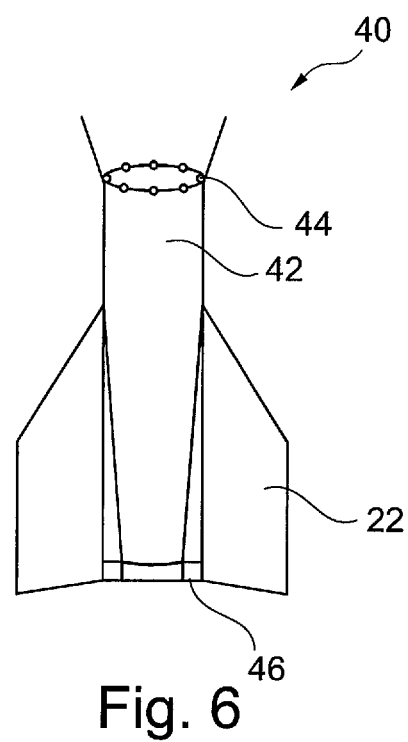
FIG. 6 is a cross-sectional view of part of the device of FIG. 5.

The proximal end 44 and closable distal end 46 can be seen for example in FIG. 6.

The proximal end 44 of the valve member 42 is secured to the support member 22 and configured to be held open thereby in the deployed condition of the device to provide a proximal opening. In the embodiment of FIGS. 5-10, the proximal end 44 of the valve member 42 is secured to the internal wall of the support member around the circumference of the proximal end 44 of the valve member 42 around an inner circumference of the internal wall at an attachment support section. Accordingly, in the deployed condition of the device, the diameter of the proximal end 44 of the valve member 42 is the same as the diameter of the attachment support section. In this embodiment, the attachment support section corresponds to the intermediate section 28 of the support member 22.

In this embodiment, the proximal end 44 of the valve member 42 is secured to the support member 22 by being attached by being sewn to the support member. However, the skilled person will appreciate that other means of securing or attaching the proximal end 44 of the valve member 42 to the support member 22 are possible, for example using a suitable adhesive.

The closable distal end of the valve member 42 in this embodiment is loose from the support member and is radially compressible and radially foldable so that, in the deployed condition of the device, flow in a proximal direction, for example against the distal end of the valve member 42, causes the distal end 46 of the valve member to be closed.

In many embodiments, the distal end 46 of the valve member is configured or designed only to open to allow components of an introducer system to be retracted, and otherwise to be closed.

As can be seen from FIG. 6, in this embodiment, the distal end 46 of the valve member 42 is substantially located at the same longitudinal position as the distal end of the support member 22. However, in other embodiments, the distal end 46 of the valve member 42 may be disposed proximally or distally to the distal end of the support member 22.

The valve member 42 in this embodiment is a tube made of conventional graft material. However, it is not excluded that other flexible materials, provided they are suitable for implantation in a human or animal body, may be used for the valve member 42.

The material of the valve member 42 is preferably substantially impermeable to blood. In addition, the internal wall of the support member is preferably substantially impermeable to blood and is preferably configured to seal against the walls of a false lumen in such a way as to prevent backflow from passing around the valve member 42. In this embodiment, this is achieved by the distal anchoring section 26 being configured to seal against the walls of a false lumen, and for the internal wall of the support member 22 to be substantially impermeable to blood at least from the proximal end 44 of the valve member 42 to the distal anchoring section 26, and preferably to the distal end of the support member 22.

In the embodiment of FIGS. 5-10, the valve member 42 includes a lumen from the proximal end 44 to the distal end 46, and the lumen tapers along the length of the valve member 42.

Accordingly, the distal end 46 of the valve member 42 is openable to a maximum distal opening which is smaller than the proximal opening at the proximal end 44 of the valve member 42.

In this embodiment, the taper provides a substantially conical shape to the lumen of the valve member 42.

Figure 7:
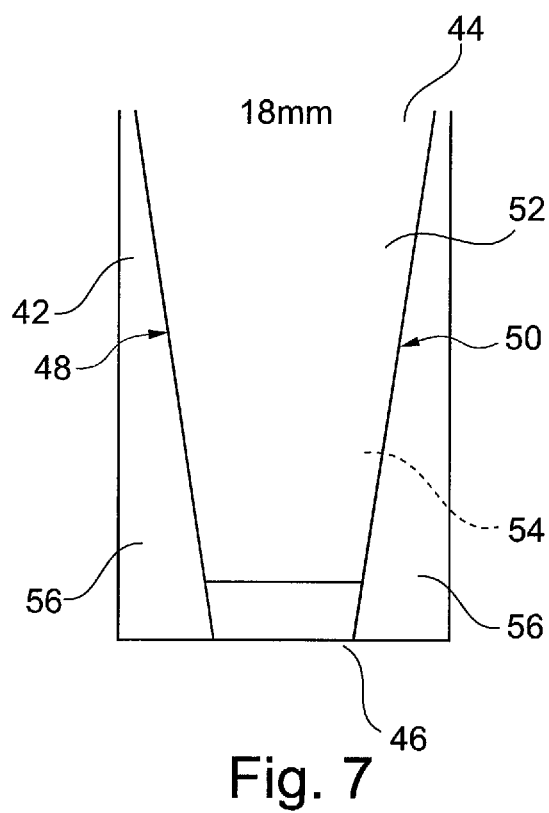
FIG. 7 is a schematic view of the valve member of the device of FIGS. 5 to 6.
Figure 8:
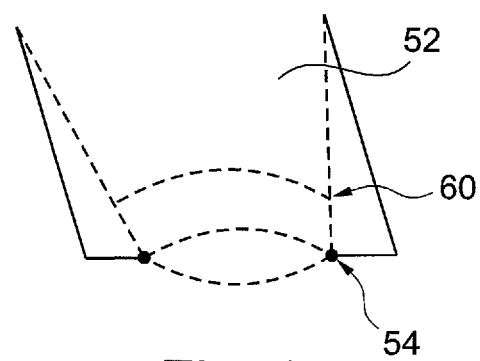
FIG. 8 is a perspective view of the valve member of the embodiment of FIGS. 5 to 7.

FIG. 7 shows in more detail the tapering of the lumen of the valve member 42.

As can be seen from FIG. 7, in this embodiment, the valve member 42 tapers in a linear fashion from the proximal end 44 to the distal end 46, although non-linear tapers are possible in other embodiments.

The valve member 42 includes a first line of attachment 48 and a second line of attachment 50. The first and second lines of attachment are provided along the length of the taper and reduce the size of the lumen by dividing a wall of the valve member 42 into a first side section 52, and a second side section 54 which decrease in size in a distal direction.

This is done by the first and second lines of attachment attaching together opposing lines of points of the valve member 42. There can be imagined to be a plane encompassing the longitudinal axis of the valve member 42 (the plane of the page in FIG. 7). The first and second lines of attachments each attach a line of points on the wall of the valve member 42 with an opposing line of points on the wall of the valve member 42 on the opposite side of the plane. The first side section 52 and the second side section 54 are therefore located on opposite sides of the plane.

FIG. 7 shows the first side section 52. The second side section 54 is on the opposite side of the valve member 42.

The first and second lines of attachment create lateral flanges 56, which are sections of the wall of the valve member 42 which are radially outside the first and second lines of attachment and therefore do not provide part of a wall of the valve member lumen.

The first and second side sections 52 and 54 therefore provide perimeter or wall sections for the lumen which are substantially the same size. However, in other embodiments, there can be first and second side sections of different sizes.

In this embodiment, the first and second lines of attachment are provided by stitching or sewing. However, other means of attachment can be used in other embodiments.

In addition, a circumferential thrombogenic element 60 is provided around the inner circumference of the lumen of the valve member 42 proximally offset from the distal end 46 of the valve member 42.

Figure 9:
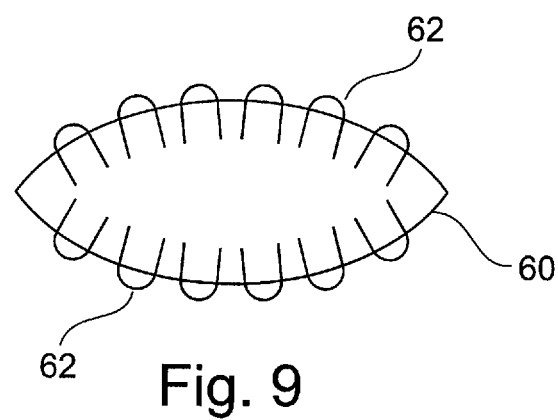
FIG. 9 is an end view of the valve member of the embodiment of FIGS. 5 to 8.
Figure 10:
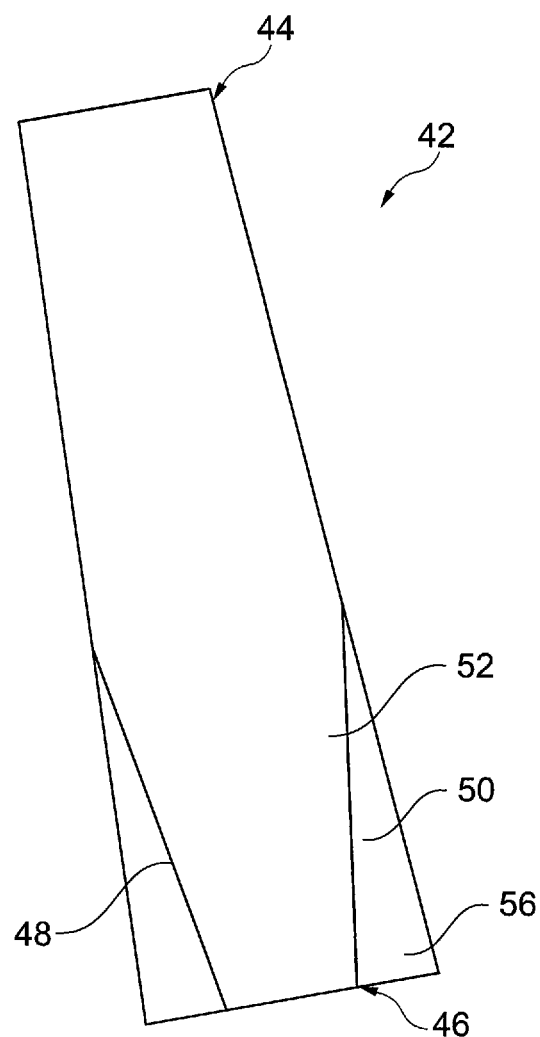
FIG. 10 shows the valve member of the embodiment of FIGS. 5 to 9.

In this embodiment, the circumferential thrombogenic element 60 is provided by thrombogenic fibres, in this embodiment nylon fibres although polyester or other thrombogenic material can be used, which are sewn by stitching 62 to an inner surface of the first and second side sections 52, 54 of the wall, as shown in FIG. 9. However, in other embodiments, thrombogenic elements can be provided elsewhere in the valve member such that they contact fluid in the lumen of the valve.

As can be seen from FIG. 5, in this embodiment, the proximal and distal anchoring sections 24, 26 have a diameter of about 30 mm to about 50 mm and the intermediate section has a diameter of about 18 mm. However, the skilled person will appreciate that the dimensions can be varied in accordance with the treatment to be carried out. In particular, although the proximal and distal anchoring sections have substantially the same diameter in this embodiment, this is not necessarily true in every embodiment.

Although not depicted, the support member of FIG. 5 includes stents as per the support member of FIG. 3. However, the skilled person will appreciate that the number and arrangement, for example whether the stents are external or internal, can be varied.

In addition, although the stents at the proximal and distal anchoring sections 24, 26 include gold markers in this embodiment, any radiopaque marker can be used, or the markers can be omitted entirely.

To use the device of FIGS. 5-10, the device is compressed into a introducer assembly in a conventional way. However, the device of FIGS. 5-10 is advantageous in that the elongate flexible tubular valve member 42 is very easily folded or radially compressed and does not significantly limit the compression of the support member 22 as some prior art candy plugs do.

During introduction, the device is introduced and deployed in a conventional way, for example as per the candy plug 20 of FIG. 2. Generally, a wire guide is advanced to the treatment site, and a delivery device is then advanced over the wire guide. The delivery device generally comprises an introducer cannula with a distal tip, and an outer sheath. The device 40 is carried in a compressed configuration between the inner cannula and outer sheath with the inner cannula passing through the valve member. Typically, a pusher member is included proximally of the device 40 to help advance the device 40 to the desired position in a conventional manner. When the device 40 is at the treatment site, the outer sheath is retracted, allowing the device 40 to expand into the deployed configuration and seal against the walls of the false lumen. The introducer system is then retracted. The distal end of the valve member 42 can open to allow the inner cannula, tip and wire guide to be retracted through the distal end of the valve member 42.

Once the device is in position, blood in the false lumen will tend to thrombose. This is because blood flowing through the tear 16 will flow against the distal end 46 of the valve member 42 and cause this to compress or fold and close, preventing proximal flow into the valve member and thereby preventing proximal flow into the false lumen. Once the blood in the false lumen has thrombosed, there is no risk for false lumen expansion and risk of rupture.

The sealing of the valve member to the support member, and the substantial impermeability of the distal part of the support member 22, prevents blood from flowing around the valve member 42 and undermining the effect of the device.

An elongate flexible tubular valve member 62 for another embodiment of the invention is shown in FIG. 11.

Although only the valve member 62 is shown in FIG. 11, in practice the valve member is secured to a support member 22 in the same manner as per the embodiment of FIGS. 5-10. In addition, all of the features and possible alternatives of the embodiment of FIGS. 5-10 apply equally to the embodiment to which FIG. 11 relates with exceptions detailed below.

In this embodiment, the device, in particular the valve member 62, includes a biasing element 66 biasing the distal end 46 of the valve member 62 to adopt a closed configuration for example to close the distal end of the valve member after components of an introducer system have been retracted through the distal end of the valve member. In any event, the distal end of the valve member is configured to close in response to proximal flowing back flow flowing against the distal end of the valve member.

In this embodiment, the biasing element includes a first Nitinol wire 68 on a first side of the valve member 62, and a second Nitinol wire 70 on a second side of the valve member 62.

FIG. 12 provides an end on view of the distal end 46 of the valve member 62 showing the first and second Nitinol wires 68, 70.

As can be seen from FIGS. 11 and 12, the first Nitinol wire 68 is associated with the first side section 52, and the second Nitinol wire 70 is associated with the second side section 54. However, as can be seen in FIGS. 11 and 12, the first and second Nitinol wires extend over both the first and second side sections and the flanges 56 to the lateral extremities of the valve member 62.

The first and second Nitinol wires are configured so that in a deployed condition of the device, the first and second Nitinol wires 68, 70 are biased to adopt a closed configuration. In other words, they are biased to close an opening between them, which opening is preferably in a central region of the valve member 62.

The first and second Nitinol wires 68, 70 are attached to the distal end 46 of the valve member 62, for example by adhesive or sewing or other means. Therefore, the first and second Nitinol wires 68, 70 bias the distal end 46 of the valve member to adopt a closed configuration.

The device of this embodiment is used in the same manner as for the embodiment of FIGS. 5-10. However, in this embodiment the first and second Nitinol wires 68, 70 assist with closing the distal end 46 of the valve member 62 for example after components of an introducer system have been retracted through the distal end of the valve member. In any event, the distal end 46 of the valve member 62 is still configured to close in response to proximal flowing back flow flowing against the distal end 46 of the valve member 62.

In other embodiments, the first and second wires 68, 70 do not need to be made of Nitinol, but could be made of other shape memory materials, or indeed other materials which can be biased to adopt a closed configuration, for example materials with spring characteristics.

In addition, although the first and second wire 68, 70 in FIG. 11 extend across the first and second wall sections and the flanges, in other embodiments, the first and second wires may be present only on the side sections 52, 54.

In other embodiments, the first and second wires 68, 70 may be replaced or enhanced by a single wire around the circumference of the lumen of the valve member 62, around the perimeter of the valve member 62, or around a part of the circumference of the lumen or a part of the perimeter of the valve member 62.

Although FIG. 11 shows the biasing member 66 as being present at the distal end 46 of the valve member 62, it could be offset therefrom. However, presence at the distal end of the valve member 62 is preferred to provide optimal closure to the distal end 60, 46 of the valve member 62.

The valve member 82 relating to another embodiment is shown in FIG. 13. This embodiment corresponds to the embodiment to which FIGS. 11 and 12 relate, except that the biasing member 86 is provided by first and second magnets attached to the valve member 82. The first and second magnets are configured such that opposite or attracting poles face each other so as to create an attractive force between the magnets. In this way the first and second magnets are configured to bias the distal end 46 of the valve member 82 into a closed configuration in a similar way to the embodiment to which FIGS. 11 and 12 relate. It is noted in this regard that the valve member 42 is a low flow, pressure, lumen. The magnets are biased to close an opening between them, which opening is preferably in a central region of the valve member 62.

Although there are shown first and second magnets in FIG. 13, there could be more magnets appropriately arranged to create a closing force at the distal end of the valve member 82.

In addition, as for FIGS. 11 and 12, it is possible for the first and second magnets to be offset from the distal end 46 of the valve member 82, although this is not preferred.

Figure 14:
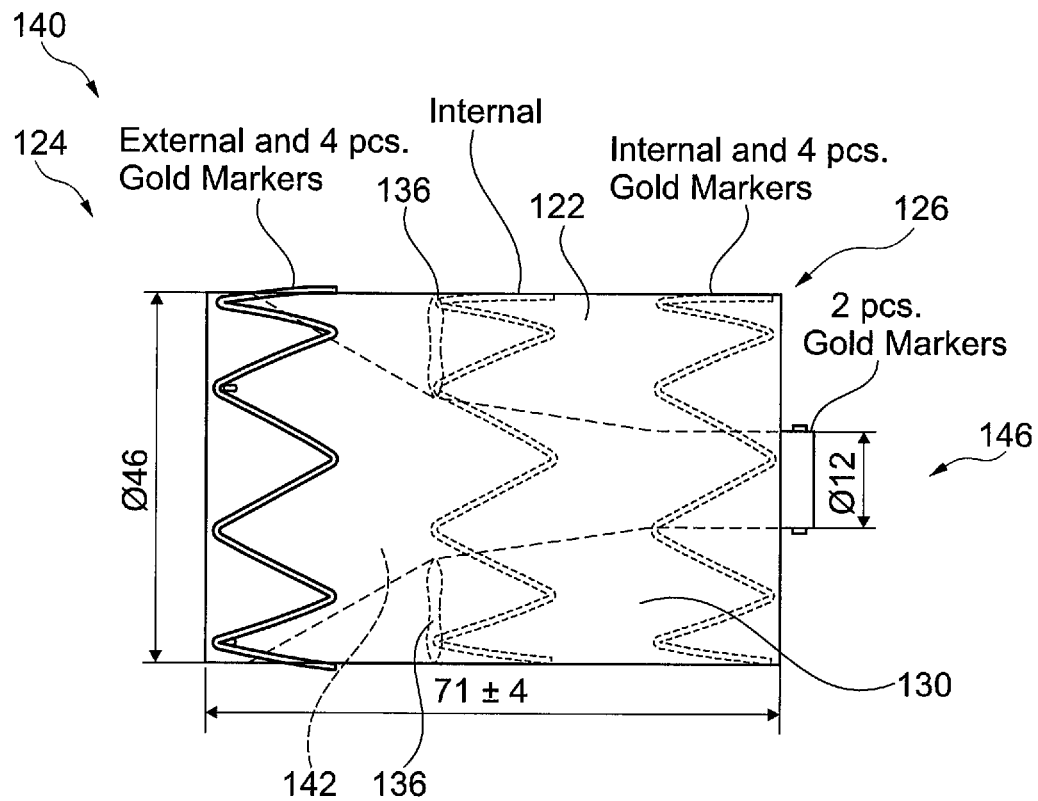
FIG. 14 is a side elevational view of a device according to another embodiment of the invention.
Figure 15:
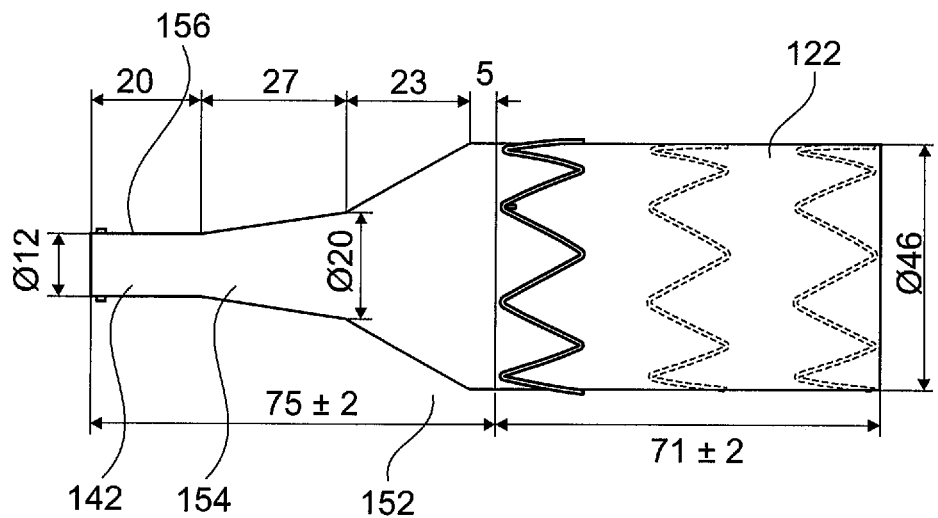
FIG. 15 is a side elevational view of the device of FIG. 14 in a pulled out form for reference.

Another embodiment of the invention is shown in FIGS. 14 and 15. Except where otherwise specified, features and modifications of the embodiment of FIGS. 14 and 15 can be the same as for other embodiments described herein.

In the embodiment of FIGS. 14 and 15, the device 140 includes an elongate support member 122 which does not have a candy plug design but is, at least in the deployed condition, substantially cylindrical.

In this embodiment, the support member 122 has in the deployed configuration a diameter of about 46 mm, and a length of about 71 mm, although these dimensions can be varied to suit the treatment and/or patient.

The support member 122 comprises a graft material tube 130 extending from a distal end 126 to a proximal end 124 and providing an internal wall to the support member, thereby forming an internal lumen. At the proximal end 124, the graft material tube 130 inverts, that is to say it turns inside itself, and passes back through the internal lumen, providing the elongate flexible valve member 142 having a proximal end at the proximal end 124 of the support member, and having a distal end 146.

The valve member 142 has as for the embodiments described above, a closable distal end such that flow in a proximal direction against the distal end causes it to be closed.

As for the valve member 42 described above, the valve member 142 tapers, in the deployed condition, from the proximal end to the distal end thereof. The degree of taper can decrease from the proximal to the distal end thereof. In this embodiment this is achieved by the degree of taper decreasing in stages; however, in other embodiments other techniques such as a non-linear taper may be used.

The tapers may be achieved by attaching opposing sides of the tube 130 in a corresponding way to that described for the embodiment of FIG. 5.

The support member 122 is provided with stents to support the internal wall and hold it against the vessel walls, and to hold open the proximal end of the valve member 142 in a deployed condition of the device. In this embodiment, there are provided three stents, a proximal external stent, a distal internal stent, and an intermediate internal stent. However, in other embodiments, different numbers of stents can be provided, and they can have different arrangements regarding whether they are internal or external.

In this embodiment, the stents are each provided with four gold markers, although this can be varied as described for the above embodiments.

The device includes a valve member positional constraint arrangement attaching the valve member 142 to the internal wall of the support member between the proximal and distal ends of the valve member. This can limit the amount the valve member 142 can move laterally and can thereby assist the valve member in remaining aligned in a substantially longitudinal direction. In this embodiment, the valve member positional constraint arrangement is provided by ties 136. In this embodiment there are two ties positioned diametrically opposite each other, although other numbers and other arrangements of ties can be provided in other embodiments.

FIG. 15 shows the device in a non-inverted state for reference. As discussed above, the internal wall of the support member 122 and the valve member 142 are made as one graft and the inner part is turned around and pulled inside. In this embodiment, the diameter of the valve member 142 tapers from 46 mm to 12 mm and has a tolerance of 4 mm.

In this embodiment, the valve member includes a first valve section 152, in this embodiment with a longitudinal length of about 23 mm, a second valve section 154, in this embodiment with a longitudinal length of about 27 mm, and a third valve section 156, in this embodiment with a longitudinal length of about 20 mm. In this embodiment, each of the first, second and third valve sections has a uniform degree of taper along its length which differs from the degree of taper of adjacent valve sections. Accordingly, in this embodiment, the first valve section 152, which is at the proximal end of the valve member 142 has a greater degree of taper than the second and third valve sections. The third valve section, which is at the distal end of the valve member 142, has a lesser degree of taper than the first and second valve sections.

The third valve section 156 in this embodiment has no taper at all and is substantially cylindrical.

In this embodiment, the first valve section tapers from a diameter of about 46 mm to a diameter of about 20 mm and the second valve section tapers from a diameter of about 20 mm to a diameter of about 12 mm, which is the diameter of the third valve section. Of course, all the dimensions can be varied to suit the patient and procedure to be performed.

Although this embodiment includes first, second and third valve sections, other embodiments may include more or fewer valve sections.

Figure 16:
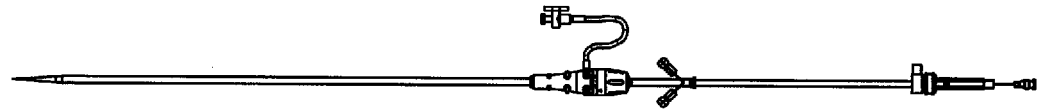
FIG. 16 is a side elevational view of a delivery device.
Figure 17:
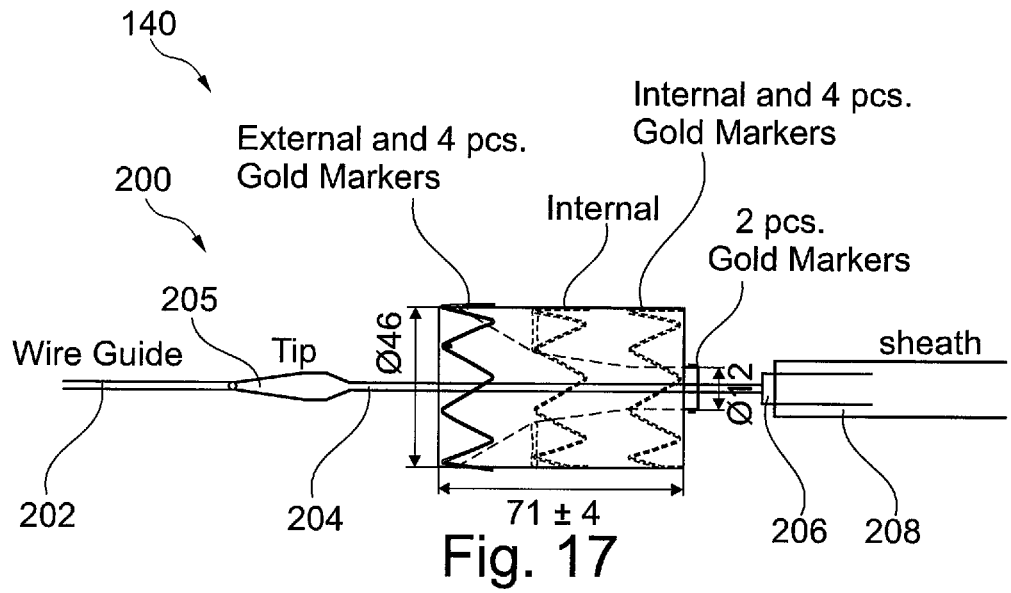
FIG. 17 is a side elevational view of the device of FIG. 14 on a delivery device.

FIG. 16 shows a delivery device suitable for use with the embodiment of FIG. 14, and FIG. 17 shows the device 140 in a deployed configuration but with the delivery device still extending through it.

As can be seen in FIG. 17, an introducer system 200 includes a wire guide 202, an inner cannula 204 with a distal tip 205, a pusher member 206, and an outer sheath 208. The device 140 is deployed in a corresponding manner to that described for the device 40. However, in the embodiment of FIGS. 14 and 15, the device is not of a candy plug design, and the support member 122 seals the aortic wall along the whole length of the support member.

Figure 18:
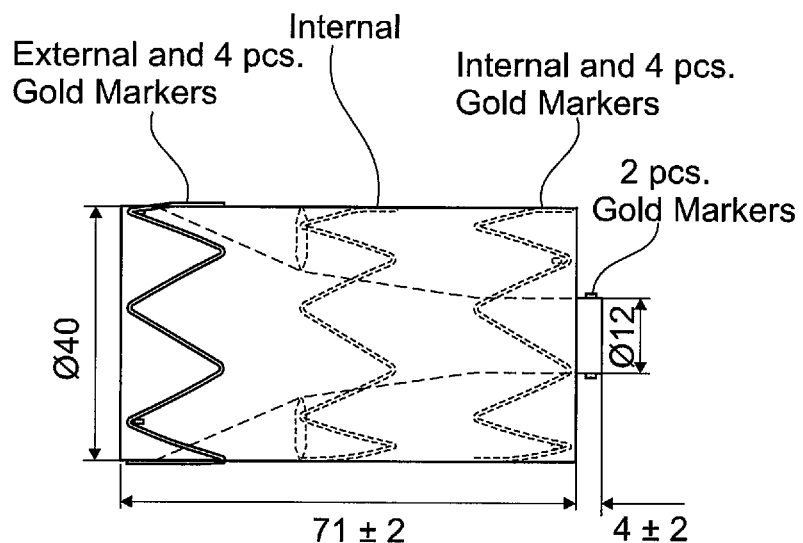
FIG. 18 is a side elevational view of a modification of the device of FIG. 14.
Figure 19:
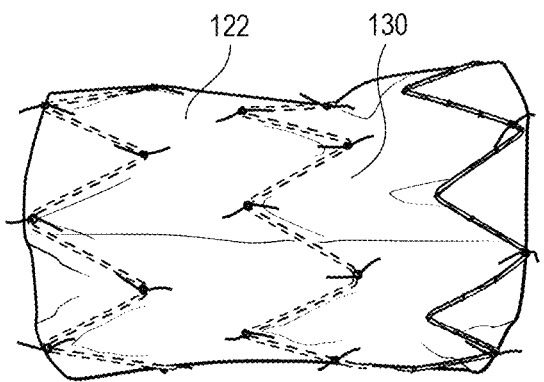
FIGS. 19-22 are views of a device according to the embodiment of FIG. 14.
Figure 20:
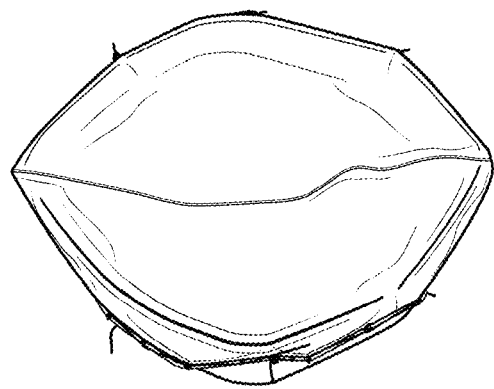
Figure 21:
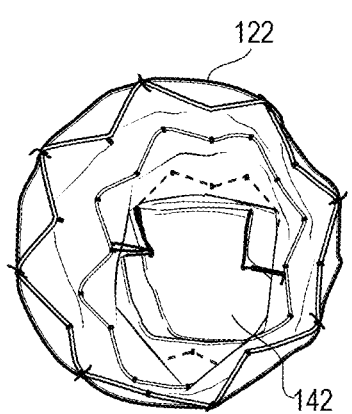
Figure 22:
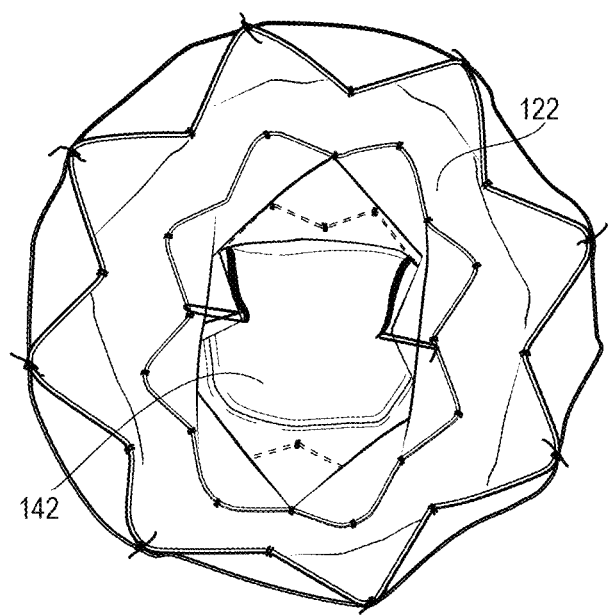

FIG. 18 shows modification of the device 140 in which the diameter is about 40 mm.

FIGS. 19 to 22 show a device according to the embodiment of FIGS. 14 and 15.

FIGS. 23 to 26 show a delivery device such as that shown in FIG. 17.

Although in the embodiments described above the valve member tapers along the entire length of the valve member 42, in some embodiments, the valve member tapers along only part of the length.

Although the embodiments described above have a taper produced by attaching opposing sides of a graft tube, in other embodiments, the graft tube can be manufactured in a tapering form.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

What is claimed is:

1. An implantable medical device for preventing backflow into a false lumen of dissection, including:
    an elongate support member including an internal wall forming an internal lumen; and
    an elongate flexible tubular valve member having a length, a proximal end, and a closable distal end, the proximal end of the valve member being secured to the support member and configured to be held open thereby in a deployed condition of the device, the valve member being at least partially unstented along its length;
    wherein in a deployed condition of the device flow in a proximal direction causes the distal end of the valve member to be closed.

2. The device of claim 1, wherein the device provides a plug.

3. The device of claim 1, wherein the distal end of the valve member is radially compressible and/or radially foldable in a deployed condition of the device to provide a valve function.

4. The device of claim 1, wherein the valve member is secured to the internal wall of the support member.

5. The device of claim 1, wherein the distal end of the valve member is loose from the support member.

6. The device of claim 1, wherein the valve member includes a graft material tube.

7. The device of claim 1, wherein the proximal end of the valve member has a proximal opening and the distal end of the valve member is openable to a maximum distal opening, wherein the maximum distal opening is smaller than the proximal opening.

8. The device of claim 1, wherein in a deployed condition of the device the valve member includes a lumen from the proximal end to the distal end, wherein the lumen tapers along at least part of the length of the valve member.

9. The device of claim 8, wherein in a deployed condition of the device the lumen along the at least part of the length of the valve member is substantially conical.

10. The device of claim 8, including first and second lines of attachment along the at least part of the length of the graft material tube, the first and second lines of attachment reducing a size of the lumen in a deployed condition of the device and dividing a wall of the valve member into a first side section and a second side section by attaching together lines of points on the wall of the valve member, the first and second lines of attachment converging towards the distal end of the valve member.

11. The device of claim 10, wherein at each cross section of the at least part of the length of the valve member, the perimeter sections provided by the first and second side sections are substantially the same size.

12. The device of claim 10, wherein the first and second lines of attachment are provided by stitching.

13. The device of claim 1, including a biasing element configured to bias the distal end of the valve member to adopt a closed configuration.

14. The device of claim 13, wherein the biasing element includes attracting magnetic elements.

15. The device of claim 13, wherein the biasing element includes a resilient member.

16. The device of claim 15, wherein the resilient member includes first and second wires comprising shape memory material.

17. The device of claim 1, wherein the internal wall of the support member is unitary with the valve member.

18. The device of claim 17, wherein the device includes a tubular member providing the internal wall of the valve member and being inverted through itself to provide the valve member.

* * * * *